US011998050B2

(12) United States Patent
Blackmon et al.

(10) Patent No.: US 11,998,050 B2
(45) Date of Patent: Jun. 4, 2024

(54) CAPSULES WITH INTERNAL CHANNELS, HEAT-NOT-BURN (HNB) AEROSOL-GENERATING DEVICES, AND METHODS OF GENERATING AN AEROSOL

(71) Applicant: Altria Client Services LLC, Richmond, VA (US)

(72) Inventors: Zack Blackmon, Williamsburg, VA (US); Patrick Good, Richmond, VA (US); Rangaraj S. Sundar, Richmond, VA (US); Jarrett Keen, Richmond, VA (US); Eric Hawes, Midlothian, VA (US); Yannick Hourmand, Haslingfield (GB); Niall Gallagher, Cambridge (GB)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 378 days.

(21) Appl. No.: 16/908,849

(22) Filed: Jun. 23, 2020

(65) Prior Publication Data

US 2021/0392954 A1     Dec. 23, 2021

(51) Int. Cl.
| | |
|---|---|
| *A24F 40/42* | (2020.01) |
| *A24F 40/20* | (2020.01) |
| *A24F 40/46* | (2020.01) |
| *A24F 40/48* | (2020.01) |
| *A61M 15/00* | (2006.01) |

(52) U.S. Cl.
CPC .............. *A24F 40/42* (2020.01); *A24F 40/20* (2020.01); *A24F 40/46* (2020.01); *A24F 40/48* (2020.01); *A61M 15/009* (2013.01); *A61M 2205/36* (2013.01)

(58) Field of Classification Search
CPC .......... A24F 40/20; A24F 40/42; A24F 40/46; A24F 40/48; A61M 15/009; A61M 2205/36

See application file for complete search history.

(56) References Cited

U.S. PATENT DOCUMENTS

| | | | | |
|---|---|---|---|---|
| 9,943,114 | B2 * | 4/2018 | Batista | ................... A24F 40/70 |
| 2001/0028119 | A1 * | 10/2001 | Wittek | ..................... A61L 9/14 |
| | | | | 261/104 |
| 2007/0062548 | A1 * | 3/2007 | Horstmann | ............. A24F 42/60 |
| | | | | 131/270 |

(Continued)

FOREIGN PATENT DOCUMENTS

EP     3393281 A1     10/2018

OTHER PUBLICATIONS

International Search Report and Written Opinion for PCT/2021/022360 dated Aug. 19, 2021.

(Continued)

*Primary Examiner* — Abdullah A Riyami
*Assistant Examiner* — Thang H Nguyen
(74) *Attorney, Agent, or Firm* — Harness, Dickey & Pierce, P.L.C.

(57) ABSTRACT

A capsule for an aerosol-generating device may include a housing defining inlet openings, outlet openings, and internal channels between the inlet openings and the outlet openings. The internal channels are configured to hold an aerosol-forming substrate. The housing is configured to facilitate a heating of the aerosol-forming substrate via conduction and/or convection so as to generate an aerosol.

21 Claims, 9 Drawing Sheets

(56) References Cited

U.S. PATENT DOCUMENTS

| | | | | |
|---|---|---|---|---|
| 2016/0106153 | A1* | 4/2016 | Zhu | A24F 40/46 |
| | | | | 392/404 |
| 2016/0143358 | A1* | 5/2016 | Zhu | A24F 40/46 |
| | | | | 392/404 |
| 2017/0311648 | A1* | 11/2017 | Gill | A24F 40/50 |
| 2018/0084831 | A1* | 3/2018 | Mironov | A24F 40/42 |
| 2018/0214645 | A1* | 8/2018 | Reevell | A24F 40/53 |
| 2018/0242644 | A1* | 8/2018 | Bessant | H05B 3/34 |
| 2018/0263286 | A1* | 9/2018 | Reevell | A24F 40/40 |
| 2020/0113235 | A1* | 4/2020 | Fernando | A24F 40/465 |
| 2022/0211101 | A1* | 7/2022 | Spieles | A24F 40/42 |

OTHER PUBLICATIONS

International Preliminary Report on Patentability for International Application No. PCT/2021/022360 dated Jan. 5, 2023.

* cited by examiner

CAPSULES WITH INTERNAL CHANNELS, HEAT-NOT-BURN (HNB) AEROSOL-GENERATING DEVICES, AND METHODS OF GENERATING AN AEROSOL

BACKGROUND

Field

The present disclosure relates to capsules, heat-not-burn (HNB) aerosol-generating devices, and methods of generating an aerosol without involving a substantial pyrolysis of the aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be tobacco. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one embodiment relates to a capsule for a heat-not-burn (HNB) aerosol-generating device. In an example embodiment, the capsule may include a housing defining inlet openings, outlet openings, and internal channels between the inlet openings and the outlet openings. The internal channels are configured to hold an aerosol-forming substrate. The housing is configured to facilitate a heating of the aerosol-forming substrate via conduction and/or convection so as to generate an aerosol.

At least one embodiment relates to a heat-not-burn (HNB) aerosol-generating device. In an example embodiment, the aerosol-generating device may include a device body and a heating assembly. The device body defines at least one slot configured to receive a capsule containing an aerosol-forming substrate. The heating assembly is configured to heat the capsule containing the aerosol-forming substrate to generate an aerosol. The heating assembly may include a first heater and a second heater configured to sandwich the capsule in between so as to heat the aerosol-forming substrate via conduction. The heating assembly may further include an upstream heater configured to heat the aerosol-forming substrate via convection.

At least one embodiment relates to a method of generating an aerosol. In an example embodiment, the method may include engaging a capsule between a first heater and a second heater. The capsule may define internal channels holding an aerosol-forming substrate. The method may additionally include heating the aerosol-forming substrate via conduction with the first heater and the second heater. Furthermore, the method may include heating the aerosol-forming substrate via convection.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
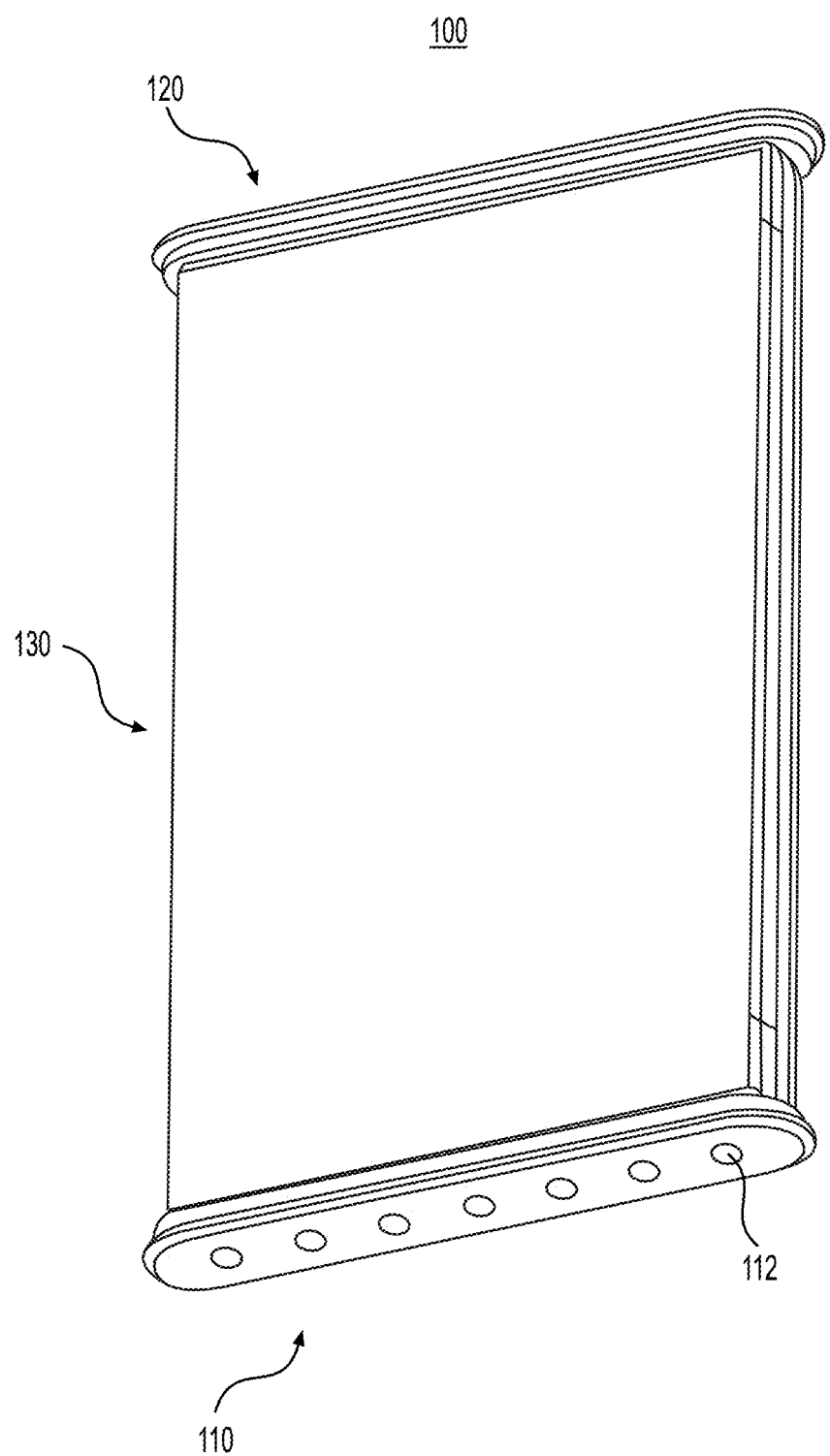
FIG. 1 is a perspective view of a capsule for an aerosol-generating device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the terms "about" or "substantially" are used in this specification in connection with a numerical value, it is intended that the associated numerical value includes a manufacturing or operational tolerance (e.g., ±10%) around the stated numerical value. Moreover, when the terms "generally" or "substantially" are used in connection with geometric shapes, it is intended that precision of the geometric shape is not required but that latitude for the shape is within the scope of the disclosure. Furthermore, regardless of whether numerical values or shapes are modified as "about," "generally," or "substantially," it will be understood that these values and shapes should be construed as including a manufacturing or operational tolerance (e.g., ±10%) around the stated numerical values or shapes.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

FIG. 1 is a perspective view of a capsule for an aerosol-generating device according to an example embodiment. Referring to FIG. 1, a capsule 100 for an aerosol-generating device includes a housing configured to hold an aerosol-forming substrate and to facilitate a heating of the aerosol-forming substrate via conduction so as to generate an aerosol. As will be discussed in more detail herein, the housing may define inlet openings for incoming air, outlet openings for outgoing aerosol, and internal channels for the aerosol-forming substrate, with the internal channels being between the inlet openings and the outlet openings.

In an example embodiment, the housing includes a body section 130, a first end cap 110, and a second end cap 120. The first end cap 110 may be secured to an upstream end of the body section 130, and the second end cap 120 may be secured to a downstream end of the body section 130 (or vice versa). In particular, the first end cap 110 and the second end cap 120 are configured to engage with the body section 130 such that each of the inlet openings of the first end cap 110 are in fluidic communication with a corresponding outlet opening of the second end cap 120 via a corresponding internal channel of the body section 130. The first end cap 110 and the second end cap 120 may be formed of a suitable plastic (e.g., via molding) or metal (e.g., via deep drawing, such as deep drawn aluminum). As used herein, "upstream" (and, conversely, "downstream") is in relation to a flow of the aerosol, and "proximal" (and, conversely, "distal") is in relation to an adult operator of the device during aerosol generation.

The first end cap 110 defines a plurality of first openings 112 as the inlet openings, and the second end cap 120 defines a plurality of second openings 122 (e.g., FIG. 5) as the outlet openings. The inlet openings are configured to permit air to enter the capsule 100, and the outlet openings are configured to permit the aerosol to exit the capsule 100. The body section 130 defines the internal channels, which are in fluidic communication with the inlet openings and the outlet openings. The internal channels are configured to hold the aerosol-forming substrate and to extend along a longest dimension of the housing.

The capsule 100 may have a slab-like form to facilitate a heating of the aerosol-forming substrate therein via conduction. For instance, the housing may have a length, a width, and a thickness that results in the slab-like form. The length of the housing extends from the upstream end face of the capsule 100 to the downstream end face of the capsule 100 and, thus, includes the corresponding dimensions of the first end cap 110 and the second end cap 120 extending beyond the body section 130. However, it should be understood that in an instance where the first end cap 110 and the second end cap 120 are configured to be seated so as to be flush with the upstream rim and the downstream rim, respectively, of the body section 130 (so as to not extend beyond the body section 130), the length of the housing may just correspond to the length of the body section 130. The width of the housing extends orthogonally to the length and along the direction of alignment of the plurality of first openings 112 (or the plurality of second openings 122). The thickness of the housing extends orthogonally to the length and the width. As illustrated, the length of the housing is greater than the width (e.g., average width, maximum width), and the width is greater than the thickness (e.g., average thickness, maximum thickness). The internal channels defined by the body section 130 extend in a direction of the length.

Figure 2:
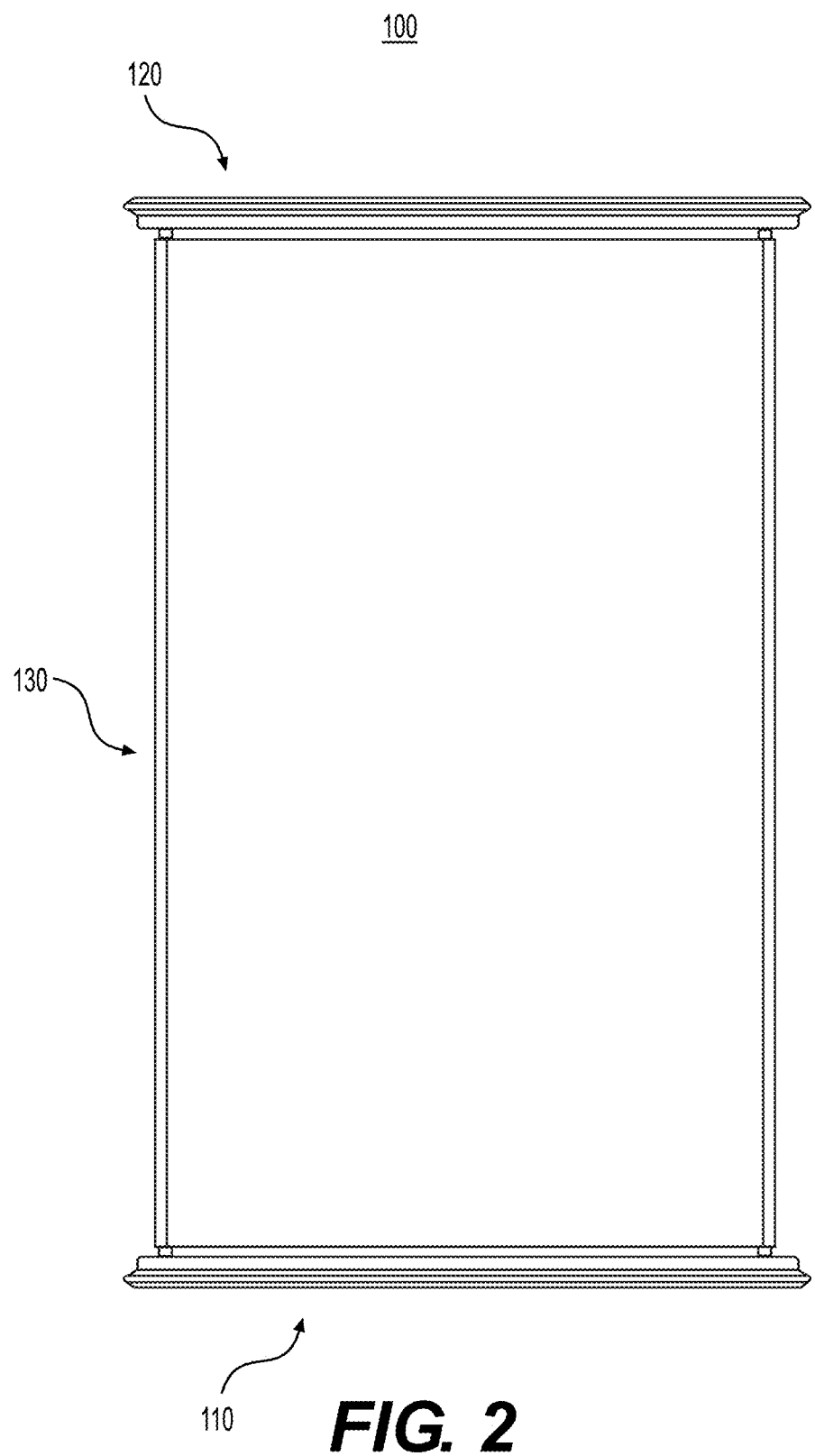
FIG. 2 is a front view of the capsule of FIG. 1.

FIG. 2 is a front view of the capsule of FIG. 1. Referring to FIG. 2, the length and the width of the housing are in view, while the thickness is not in view. With regard to the width of the housing, the portions of the housing corresponding to the first end cap 110 and the second end cap 120 are wider than the portion of the housing corresponding to the body section 130. However, in another instance, the first end cap 110 and the second end cap 120 may be configured to be even with the side walls of the body section 130. In such an instance, the width of the housing may be regarded as being uniform.

Figure 3:
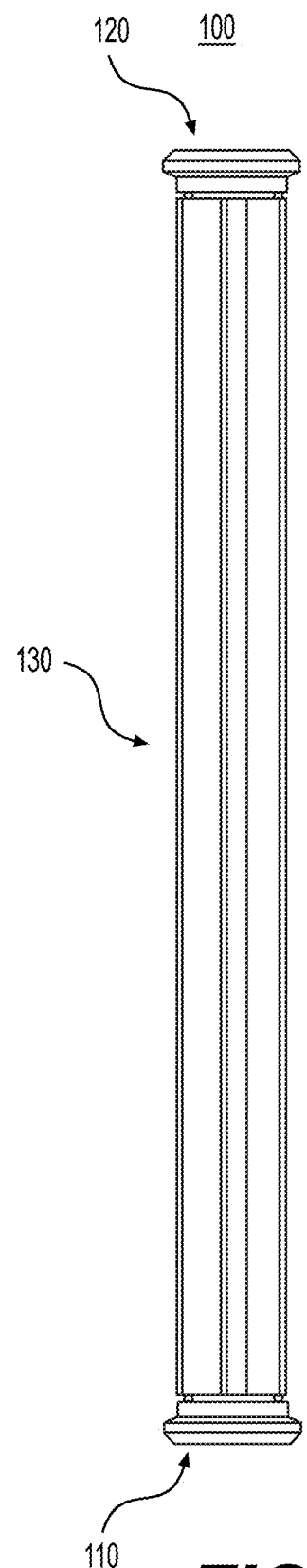
FIG. 3 is a side view of the capsule of FIG. 1.

FIG. 3 is a side view of the capsule of FIG. 1. Referring to FIG. 3, the length and the thickness of the housing are in view, while the width is not in view. With regard to the thickness of the housing, the portions of the housing corresponding to the first end cap 110 and the second end cap 120 are thicker than the portion of the housing corresponding to the body section 130. However, in another instance, the first end cap 110 and the second end cap 120 may be configured to be even with the front and rear walls of the body section 130. In such an instance, the thickness of the housing may be regarded as being uniform. In an example embodiment, the thickness of the housing is configured to facilitate the uniform heating of the aerosol-forming substrate 160 (FIG. 5) within the capsule 100.

Figure 4:
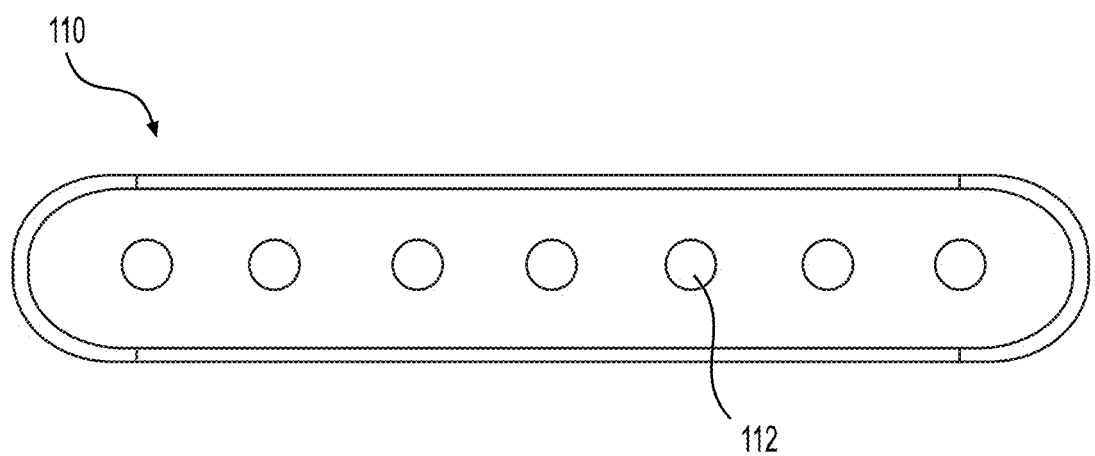
FIG. 4 is an end view of the capsule of FIG. 1.

FIG. 4 is an end view of the capsule of FIG. 1. Referring to FIG. 4, the first end cap 110 may have a shape resembling a rectangle with a pair of opposing semicircular ends (e.g., elongated circle, obround, discorectangle) based on an upstream end view of the capsule 100. However, in another instance, the first end cap 110 may have a rectangular shape with angular or rounded corners based on an upstream end view of the capsule 100. As illustrated, the plurality of first openings 112 may be evenly spaced and arranged in a linear manner. Alternatively, in some instances, the plurality of first openings 112 may be arranged in a staggered manner (e.g., zigzag arrangement). Furthermore, although the first end cap 110 is illustrated as defining seven first openings 112, it should be understood that example embodiments are not limited thereto. For instance, the first end cap 110 may define more (e.g., eight) or less (e.g., six) openings based on the number of internal channels within the capsule 100.

Figure 5:
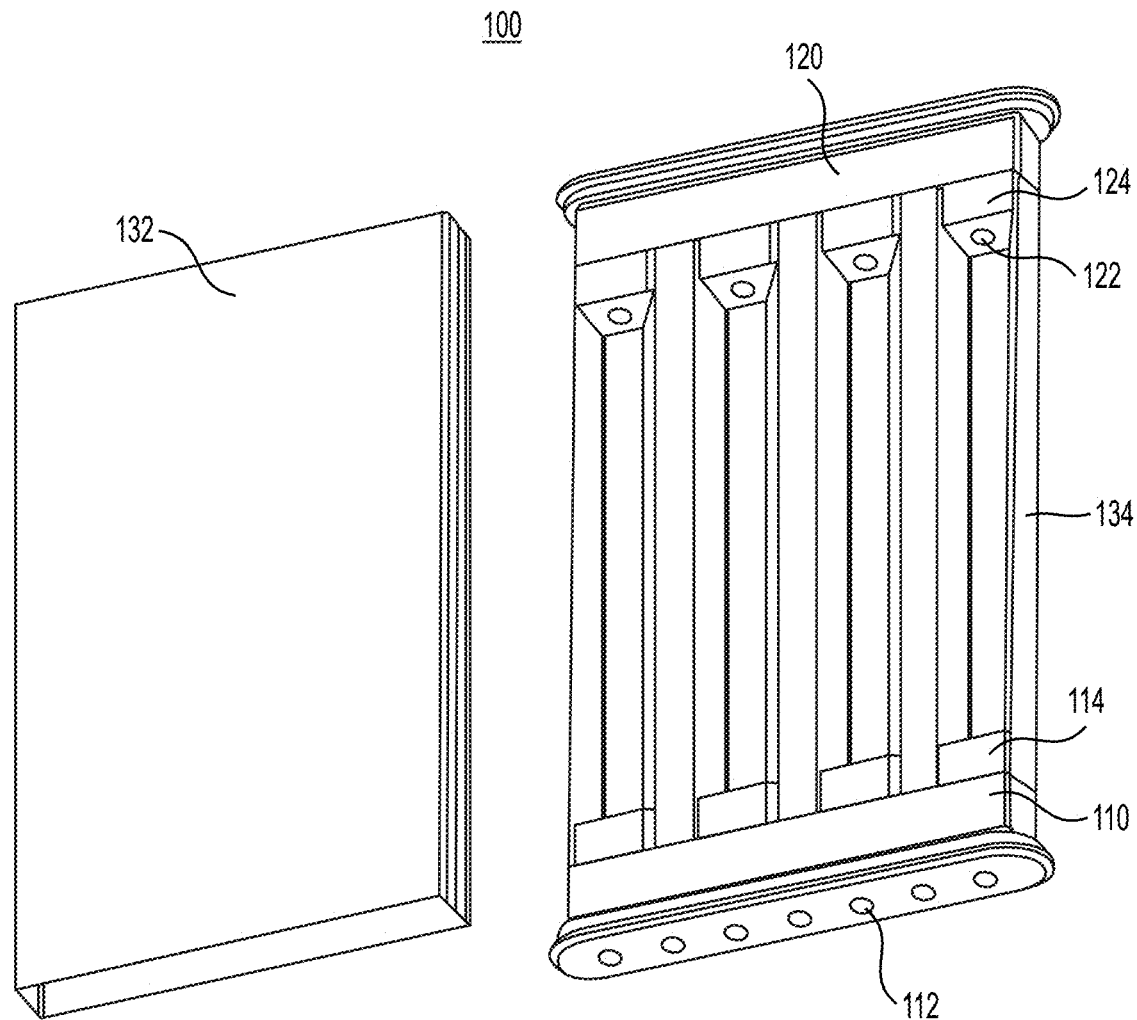
FIG. 5 is a partially exploded view of the capsule of FIG. 1.
Figure 5:
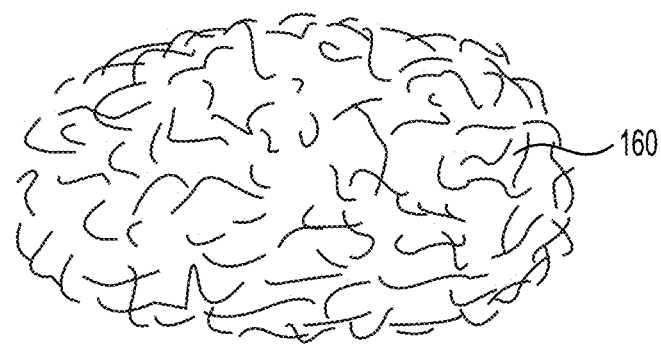

FIG. 5 is a partially exploded view of the capsule of FIG. 1. As illustrated, in addition to the first end cap 110 and the second end cap 120, the capsule 100 may also include a corrugated structure 134 and a cover 132 configured to contain the corrugated structure 134. In an example embodiment, the combination of corrugated structure 134 and the cover 132 may be regarded as the body section 130. Additionally, the cover 132 may be a conductive cover (e.g., thermally conductive cover) that facilitates a heating of the aerosol-forming substrate 160 via conduction. For instance, the cover 132 may be made of metal(s). The metal(s) may include aluminum (e.g., aluminum or alloy thereof in a form of a foil). The aluminum may also be anodized aluminum.

In FIG. 5, the cover 132 is shown separately, while the first end cap 110 and the second end cap 120 are engaged with the corrugated structure 134. The first end cap 110 includes a plurality of first mating members 114 configured to engage with the upstream end of the corrugated structure 134, while the second end cap 120 includes a plurality of second mating members 124 configured to engage with the downstream end of the corrugated structure 134. In an example embodiment, the first end cap 110 and the second end cap 120 are identical structures and, thus interchangeable. In such an instance, the first end cap 110 may be engaged with the downstream end of the corrugated structure 134, while the second end cap 120 is engaged with the upstream end of the corrugated structure 134.

Each of the plurality of first mating members 114 has one of the plurality of first openings 112 extending therethrough, while the remainder of the plurality of first openings 112 extend through adjacent portions of the first end cap 110 between the plurality of first mating members 114. Similarly, each of the plurality of second mating members 124 has one of the plurality of second openings 122 extending therethrough, while the remainder of the plurality of second openings 122 extend through adjacent portions of the second end cap 120 between the plurality of second mating members 124 (e.g., hidden from view in FIG. 5 but shown in FIG. 7).

Figure 6:
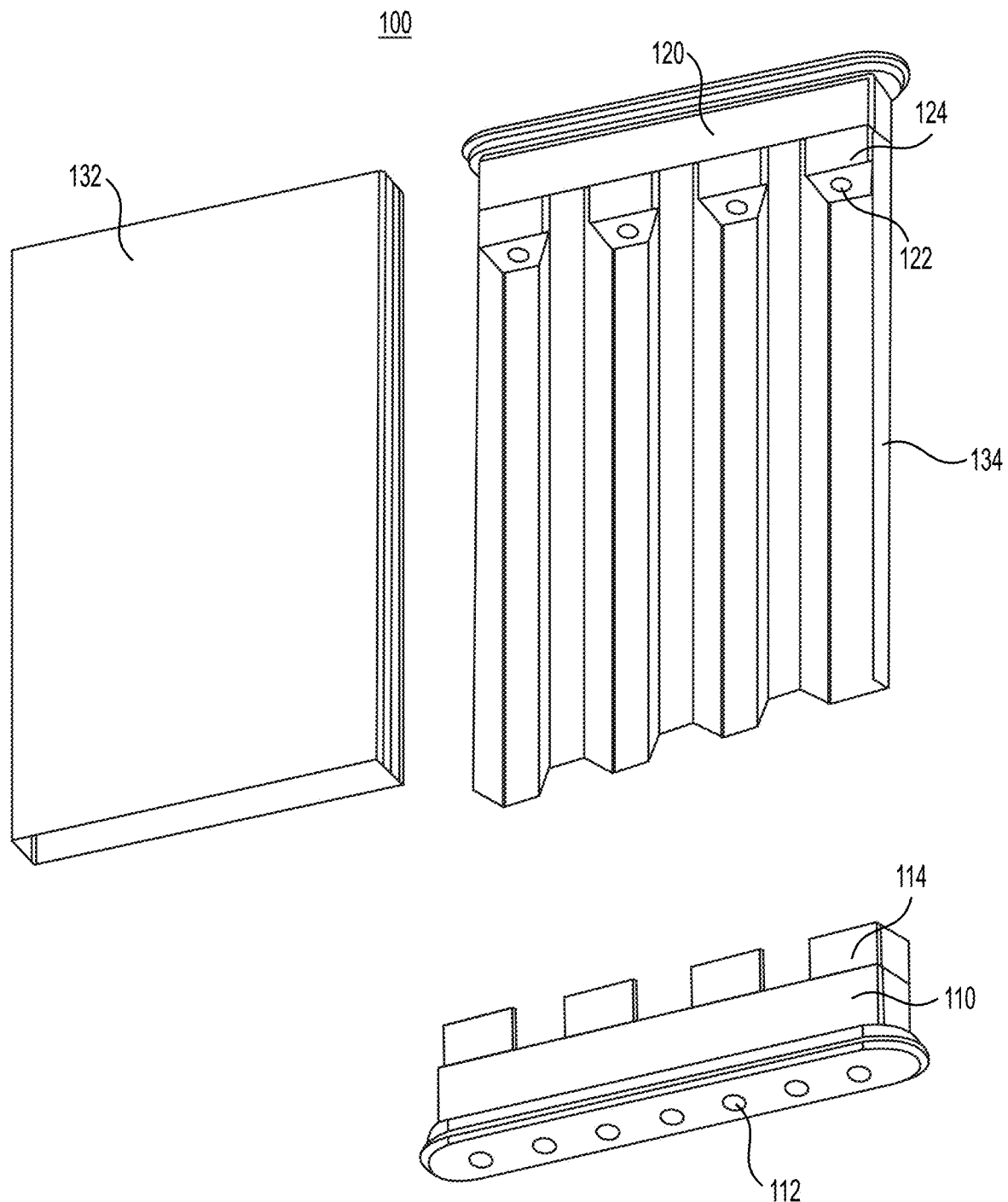
FIG. 6 is an additionally exploded view of the capsule of FIG. 5.

FIG. 6 is an additionally exploded view of the capsule of FIG. 5. Referring to FIG. 6, the first end cap 110 is disengaged from the upstream end of the corrugated structure 134, while the second end cap 120 is engaged with the downstream end of the corrugated structure 134. Each of the plurality of first mating members 114 and the plurality of second mating members 124 has a shape configured for seating within a corresponding furrow or trough of the corrugated structure 134. When seated, each of the plurality of first mating members 114 and the plurality of second mating members 124 may also be separated from an adjacent mating member by a ridge or crest of the corrugated structure 134.

As illustrated, the corrugated structure 134 may have a cross-section resembling a trapezoidal wave. In such an instance, each of the plurality of first mating members 114 and the plurality of second mating members 124 may have an inverted trapezoidal shape (e.g., inverted isosceles trapezoid) configured for seating within a corresponding furrow or trough of the corrugated structure 134 (based on the orientation shown in FIG. 6). Additionally, the plurality of first mating members 114 and the plurality of second mating members 124 on the ends may have an inverted right-angled trapezoidal shape. Thus, the plurality of first mating members 114 may include two mating members that have an inverted isosceles trapezoidal shape and two mating members that have an inverted right-angled trapezoidal shape, while the plurality of second mating members 124 may similarly include two mating members that have an inverted isosceles trapezoidal shape and two mating members that have an inverted right-angled trapezoidal shape. However, it should be understood that other configurations are also possible. For instance, alternatively, the corrugated structure 134 may have a cross-section resembling a square wave, a triangle wave, a sawtooth wave, or a sine wave, and the plurality of first mating members 114 and the plurality of second mating members 124 may be shaped accordingly.

Figure 7:
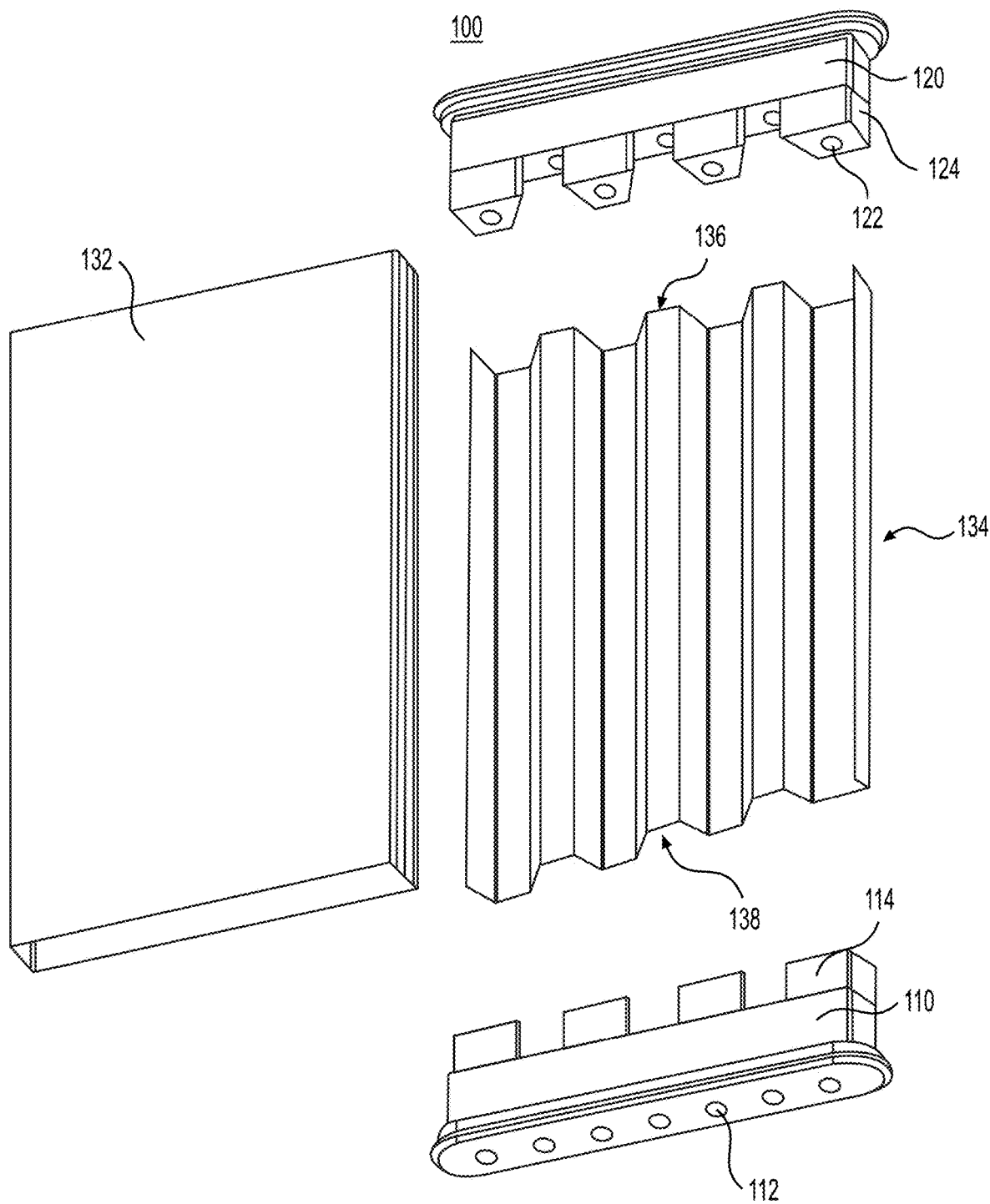
FIG. 7 is a further exploded view of the capsule of FIG. 6.

FIG. 7 is a further exploded view of the capsule of FIG. 6. Referring to FIG. 7, the corrugated structure 134 is disengaged from both the first end cap 110 and the second end cap 120. The corrugated structure 134 has alternating ridges 136 and furrows 138 as the internal channels configured to hold the aerosol-forming substrate. In an example embodiment, the internal channels provided by the ridges 136 and furrows 138 are separate and independent conduits. It should be understood that a ridge 136 on the front side of the corrugated structure 134 shown in FIG. 7 would be a furrow 138 on the rear side of the corrugated structure 134. Conversely, a furrow 138 on the front side of the corrugated structure 134 shown in FIG. 7 would be a ridge 136 on the rear side of the corrugated structure 134.

In an example embodiment, the front side of the corrugated structure 134 shown in FIG. 7 has three ridges 136 and four furrows 138, while the rear side of the corrugated structure 134 has four ridges 136 and three furrows 138. In such an instance, the corrugated structure 134 defines seven internal channels which correspond to the first openings 112 (seven total) in the first end cap 110 and the second openings 122 (seven total) in the second end cap 120. In particular, four internal channels may be provided by the four furrows 138 on the front side of the corrugated structure 134 shown in FIG. 7, while three internal channels may be provided by the three furrows 138 on the rear side of the corrugated structure 134.

As illustrated, each of the ridges 136 and furrows 138 of the corrugated structure 134 may have a coplanar surface between a pair of angled surfaces. For instance, the coplanar surfaces on the front side of the corrugated structure 134 shown in FIG. 7 may be in the form of three ridge top strips and four furrow bottom strips extending between the first end cap 110 and the second end cap 120. Similarly, the coplanar surfaces on the rear side of the corrugated structure 134 may be in the form of four ridge top strips and three furrow bottom strips extending between the first end cap 110 and the second end cap 120. The coplanar strips may extend in parallel. It should be understood that the top portions of the ridges 136 on the front side of the corrugated structure 134 shown in FIG. 7 will be the bottom portions of the furrows 138 on the rear side of the corrugated structure 134. Conversely, the bottom portions of the furrows 138 on the front side of the corrugated structure 134 shown in FIG. 7 will be the top portions of the ridges 136 on the rear side of the corrugated structure 134.

The corrugated structure 134 is formed of a suitable material having sufficient rigidity to maintain the integrity of the ridges 136 and the furrows 138 when the aerosol-forming substrate is loaded into the internal channels of the capsule 100. For instance, the corrugated structure 134 may be formed of a plant-based sheet material (e.g., cardboard such as concertina cardboard, paperboard, or molded pulp). The plant-based sheet material may be fabricated from wood, bamboo, tobacco, and/or *cannabis* (e.g., bamboo and tobacco pulp). In another instance, the corrugated structure 134 may be formed of plastic or metal.

The cover 132 is configured to receive the corrugated structure 134 so as to surround the ridges 136 and furrows 138 when the capsule 100 is assembled. In an example embodiment, the ridges 136 and the furrows 138 are configured to contact the opposing inner surfaces of the cover 132 when the corrugated structure 134 is received within the cover 132. The opposing end folds of the corrugated structure 134 may also contact the opposing inner sidewalls of the cover 132 when the corrugated structure 134 is received within the cover 132. As a result, the corrugated structure 134 may have nine sections of contact with the cover 132, although example embodiments are not limited thereto. Additionally, the cover 132 is configured to receive the first end cap 110 and the second end cap 120 such that at least the first mating members 114 and the second mating members 124, respectively, are within the cover 132 and, thus, hidden from view when the capsule 100 is assembled. As illustrated, the cover 132 may be in a form of a box sleeve.

To assemble the capsule 100, the first end cap 110 may be engaged with the corrugated structure 134 such that each of the plurality of first mating members 114 is seated within a corresponding furrow 138. The corrugated structure 134 and the first end cap 110 may then be inserted into the cover 132 until the flanged portion of the first end cap 110 abuts the upstream rim of the cover 132. Alternatively, the corrugated structure 134 may be initially received within the cover 132 before the first end cap 110 is inserted to engage both the corrugated structure 134 and the cover 132. In either instance, a portion of the upstream end of the corrugated structure 134 may be between (e.g., pressed between) the plurality of first mating members 114 and the cover 132. The engagement between the first end cap 110 and the cover 132 may be via an interference fit (which may also be referred to as a press fit or friction fit). Furthermore, in lieu of or in addition to the interference fit, the first end cap 110 may also be secured to the cover 132 with an adhesive (e.g., glue) that has been deemed food-safe or otherwise acceptable by a regulatory authority.

Once the corrugated structure 134 and the first end cap 110 are engaged with the cover 132, an aerosol-forming substrate may then be loaded into the internal channels. As noted supra, the internal channels are defined by the body section 130, which includes the cover 132 and the corrugated structure 134. In particular, each internal channel may be regarded as being defined by a furrow 138 of the corrugated structure 134 and a corresponding inner surface of the cover 132. As a result, the four furrows 138 on the front side of the corrugated structure 134 shown in FIG. 7 and the corresponding inner surfaces of the cover 132 define four internal channels, while the three furrows 138 on the rear side of the corrugated structure 134 and the corresponding inner surfaces of the cover 132 define three internal channels. In this manner, seven internal channels may be defined by the corrugated structure 134 and the cover 132.

In an example embodiment, one type of aerosol-forming substrate may be loaded into the capsule 100. In such an instance, the same aerosol-forming substrate may be loaded into each of the internal channels defined by the body section 130 of the capsule 100. In another example embodiment, several types of aerosol-forming substrates may be loaded into the capsule 100. For instance, a first type of aerosol-forming substrate may be loaded into a first group of the internal channels (e.g., four internal channels on the front side of the corrugated structure 134 shown in FIG. 7), while a second type of aerosol-forming substrate may loaded into a second group of the internal channels (e.g., three internal channels on the rear side of the corrugated structure 134). In yet another example embodiment, a mixture of different types of aerosol-forming substrates may be loaded into the same internal channel for one or more of the internal channels defined by the body section 130 of the capsule 100. However, it should be understood that example embodiments are not limited thereto and that other combinations are possible.

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *cannabis* plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from a heater may cause decarboxylation so as to convert the tetrahydrocannabinolic acid (THCA) in the capsule 100 to tetrahydrocannabinol (THC), and/or to convert the cannabidiolic acid (CBDA) in the capsule 100 to cannabidiol (CBD).

In instances where both tetrahydrocannabinolic acid (THCA) and tetrahydrocannabinol (THC) are present in the capsule 100, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 100. Similarly, in instances where both cannabidiolic acid (CBDA) and cannabidiol (CBD) are present in the capsule 100, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule 100.

Furthermore, the compound may be or may additionally include a non-naturally occurring additive that is subsequently introduced into the fibrous material. In one instance, the fibrous material may include at least one of cotton, rayon, a combination thereof, or the like (e.g., in a form of a gauze). In another instance, the fibrous material may be a cellulose material (e.g., non-tobacco and/or non-*cannabis* material). In either instance, the compound introduced may include nicotine, cannabinoids, and/or flavorants. The flavorants may be from natural sources, such as plant extracts (e.g., tobacco extract, *cannabis* extract), and/or artificial sources. In yet another instance, when the fibrous material includes tobacco and/or *cannabis*, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of *cannabis* may be increased through supplementation with an extract containing such cannabinoids.

After the loading of the aerosol-forming substrate into the internal channels, the second end cap 120 is inserted into the cover 132 to engage with the corrugated structure 134. In particular, the second end cap 120 may be inserted into the cover 132 until the flanged portion of the second end cap 120 abuts the downstream rim of the cover 132. Additionally, a portion of the downstream end of the corrugated structure 134 may be between (e.g., pressed between) the plurality of second mating members 124 and the cover 132. The engagement between the second end cap 120 and the cover 132 may be via an interference fit. Furthermore, in lieu of or in addition to the interference fit, the second end cap 120 may also be secured to the cover 132 with an adhesive that has been deemed food-safe or otherwise acceptable by a regulatory authority.

When the capsule 100 is assembled, the second mating members 124 of the second end cap 120 will be seated within the same furrows 138 of the corrugated structure 134 as the first mating members 114 of the first end cap 110. As a result, the first openings 112 extending through the first mating members 114 of the first end cap 110 will be in fluidic communication with the second openings 122 extending through the second mating members 124 of the second end cap 120. Similarly, the first openings 112 extending between the first mating members 114 of the first end cap 110 will be in fluidic communication with the second openings 122 extending between the second mating members 124 of the second end cap 120. Accordingly, during aerosol generation, incoming air entering the capsule 100 via a first opening 112 in the first end cap 110 will flow through a corresponding internal channel and the aerosol-forming substrate being heated therein, thereby entraining the volatiles released from the aerosol-forming substrate to produce an aerosol that is drawn out of the capsule 100 via a corresponding second opening 122 in the second end cap 120 at the opposite downstream end of the internal channel. In this manner, seven separate and independent air/aerosol streams may be regarded as flowing through the capsule 100 during aerosol generation by virtue of the seven internal channels defined therein.

Although the assembly process above for the capsule 100 has been discussed as concluding with the engagement of the second end cap 120 with the cover 132 and the corrugated structure 134, it should be understood that the assembly process may be reversed so as to instead conclude with the engagement of the first end cap 110 with the cover 132 and the corrugated structure 134. In any event, once assembled, the capsule 100 may be as shown in FIG. 1. While not illustrated, a sealing strip may also be applied to each of the upstream end face of the first end cap 110 and the downstream end face of the second end cap 120 so as to cover the first openings 112 and the second openings 122, respectively, (e.g., in preparation for or during packaging) for the purpose of preserving the organoleptic properties of the aerosol-forming substrate.

Figure 8:
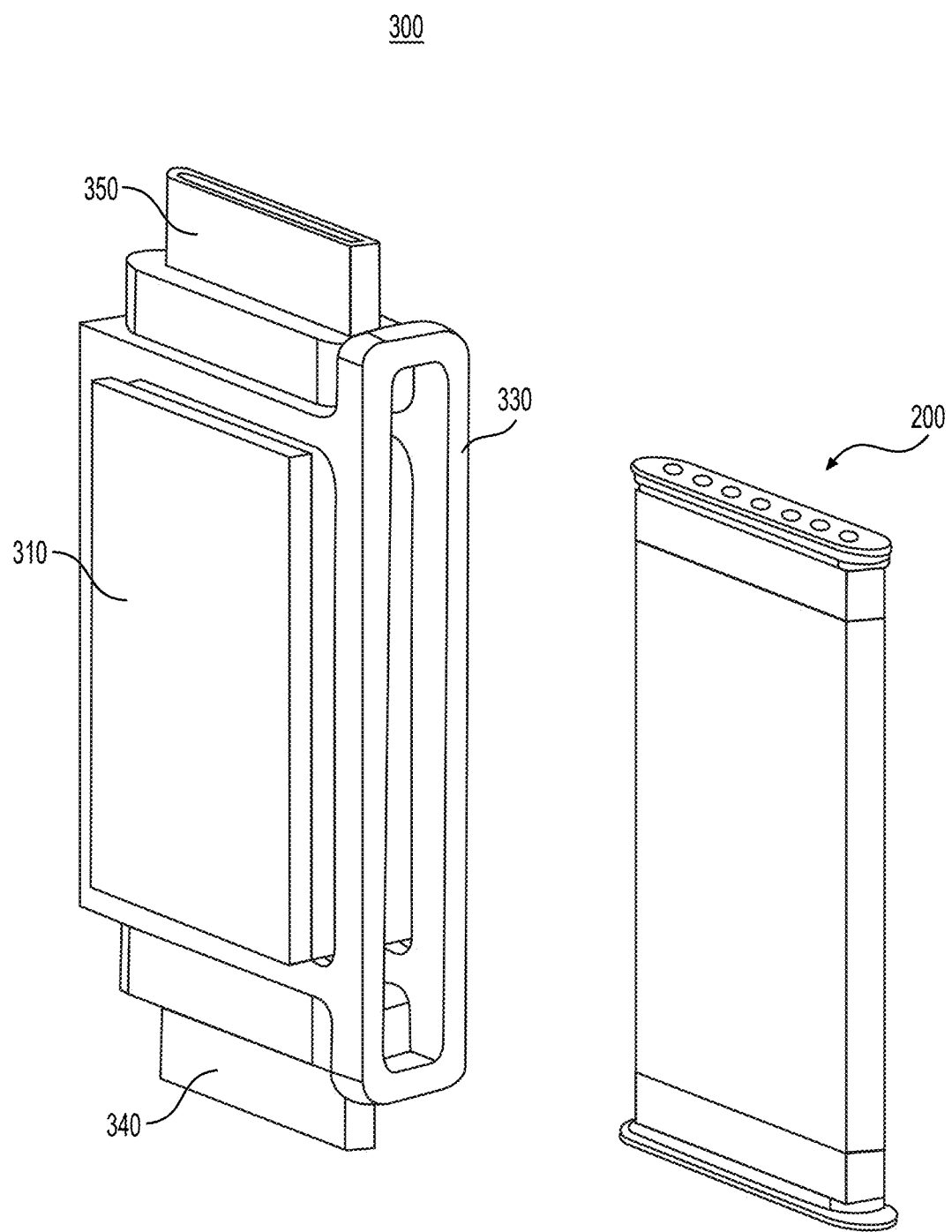
FIG. 8 is a perspective view of an aerosol-generating device according to an example embodiment.

FIG. 8 is a perspective view of an aerosol-generating device according to an example embodiment. Referring to FIG. 8, an aerosol-generating device 300 includes a device body 330 defining at least one slot configured to receive a capsule 200 containing an aerosol-forming substrate. The aerosol-generating device 300 additionally includes a heating assembly configured to heat the capsule 200 and the aerosol-forming substrate therein to generate an aerosol. The heating assembly may include a first heater 310 and a second heater 320 (FIG. 9) configured to sandwich the capsule 200 in between so as to heat the aerosol-forming substrate via conduction. The first heater 310 and the second heater 320 may be configured to operate jointly or independently (e.g., so as to be capable of providing different heating profiles). Furthermore, the aerosol-generating device 300 may include a first coupler 340 defining an air inlet and a second coupler 350 defining an aerosol outlet. The capsule 200 in FIG. 8 may be the same as the capsule 100 in FIGS. 1-7. As a result, the relevant disclosures above of the features in common should be understood to apply to this section and may not have been repeated in the interest of brevity.

Figure 9:
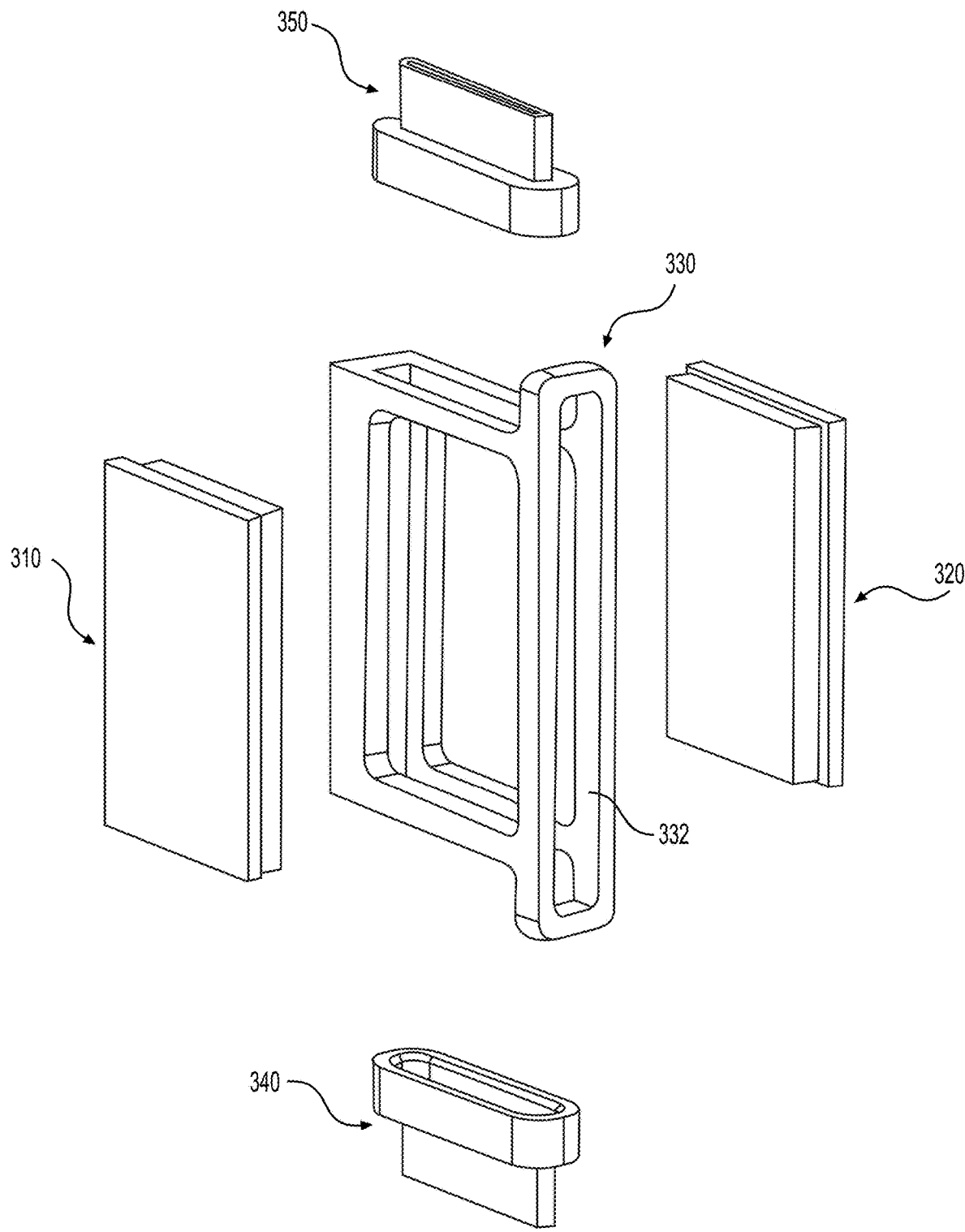
FIG. 9 is an exploded view of the aerosol-generating device of FIG. 8.

FIG. 9 is an exploded view of the aerosol-generating device of FIG. 8. Referring to FIG. 9, the device body 330 of the aerosol-generating device 300 defines a slot 332 (e.g., side slot for side loading) configured to receive the capsule 200 (FIG. 8). Additionally, the device body 330 of the aerosol-generating device 300 may define a front opening and a rear opening configured to expose the front and the rear, respectively, of the cover of the capsule 200 (when the capsule 200 is received within the device body 330) so as to permit an engagement with the first heater 310 and the second heater 320, respectively. The device body 330 may also define an upstream opening (e.g., upstream slot) and a downstream opening (e.g., downstream slot) configured to accommodate the first end cap and the second end cap, respectively, of the capsule 200 so as to permit an engagement with the first coupler 340 and the second coupler 350, respectively. In an example embodiment, the capsule 200 may, alternatively, be inserted into the device body 330 through the upstream opening (e.g., bottom loading) and/or the downstream opening (e.g., top loading).

The cover, the first end cap, and the second end cap of the capsule 200 may be as described in connection with the cover 132, the first end cap 110, and the second end cap 120 of the capsule 100. Although not illustrated, it should be understood that the capsule 200 may also include a corrugated structure within, which may be as described in connection with the corrugated structure 134 of the capsule 100. As a result, the applicable details already discussed above will not be repeated in the interest of brevity.

In an example embodiment, the capsule 200 may be inserted into the slot 332 such that the capsule 200 abuts the opposing closed side of the device body 330. The capsule 200 may then be engaged by the first coupler 340 and the second coupler 350. The first coupler 340 may define an elongated, narrow opening (e.g., first slit) configured to coincide with at least the first openings in the first end cap of the capsule 200. For instance, the length of the elongated, narrow opening of the first coupler 340 may be greater than the linear span of the collective first openings in the first end cap of the capsule 200. Additionally, the width of the elongated, narrow opening of the first coupler 340 may be less than the diameter of the first openings in the first end cap of the capsule 200. During the operation of the aerosol-generating device 300, incoming air passes through the elongated, narrow opening of the first coupler 340 and then enters the capsule 200 via the first openings in the first end cap.

Similarly, the second coupler 350 may define an elongated, narrow opening (e.g., second slit) configured to coincide with at least the second openings in the second end cap of the capsule 200. For instance, the length of the elongated, narrow opening of the second coupler 350 may be greater than the linear span of the collective second openings in the second end cap of the capsule 200. Additionally, the width of the elongated, narrow opening of the second coupler 350 may be less than the diameter of the second openings in the second end cap of the capsule 200. During the operation of the aerosol-generating device 300, the generated aerosol exits the capsule 200 via the second openings in the second end cap and then continues through the elongated, narrow opening of the second coupler 350. From a structural perspective, the second coupler 350 may be identical to the first coupler 340, although example embodiments are not limited thereto.

The first heater 310 and the second heater 320 are configured to physically contact the cover of the capsule 200 when the capsule 200 is fully engaged within the aerosol-generating device 300. In an example embodiment, the first heater 310 and the second heater 320 may additionally overlap with the first end cap and the second end cap of the capsule 200 without physically contacting the first end cap and the second end cap (by virtue of the intervening cover of the capsule 200). Furthermore, the engaging, inner surface of the first heater 310 is configured to interface with a majority (e.g., at least 80%) of the first face (e.g., front face) of the cover of the capsule 200. Similarly, the engaging, inner surface of the second heater 320 may be configured to interface with a majority (e.g., at least 80%) of the opposing second face (e.g., rear face) of the cover of the capsule 200. As a result, a desirable level of thermal contact may be established to heat the aerosol-forming substrate within the capsule 200 via conduction to generate an aerosol.

The first heater 310 and the second heater 320 may utilize resistive heating elements and may be embodied as ceramic, silicone, wire, or mesh heaters as known in the art. From a structural perspective, the first heater 310 may be identical to the second heater 320, although example embodiments are not limited thereto. Furthermore, in some instances, the aerosol-generating device 300 may be configured such that the incoming air initially flows along the outer surface of the first heater 310 and/or the outer surface of the second heater 320 (e.g., in a direction from the second coupler 350 to the first coupler 340) before passing through the first coupler 340. In another instance, a separate upstream heater may be provided to heat the incoming air before it passes through the first coupler 340. In either instance, the incoming air may be heated (e.g., pre-heated) before passing through the first coupler 340 and into the capsule 200 to heat the aerosol-forming substrate therein via convection.

While not illustrated, it should be understood that the aerosol-generating device 300 may include additional structures/components configured to provide the desired aesthetics and/or functionalities. For instance, the aerosol-generating device 300 may include an external housing structure that is designed to be visually appealing while sized to be portable and configured to facilitate ease of handling (e.g., ergonomically-shaped for one-handed operation). Also, within the external housing structure may be provided actuating mechanisms, a power source, and control circuitry. The actuating mechanisms (e.g., rack and pinion arrangements and/or spring-loaded arrangements) may be configured to move the first coupler 340, the second coupler 350, the first heater 310, and/or the second heater 320 so as to engage the capsule 200. The actuating mechanisms may also provide a confirmatory feedback (e.g., audible click) to indicate that the capsule 200 is properly inserted and engaged (e.g., locked-in). The power source may include one or more batteries (e.g., rechargeable battery arrangement). Upon engagement of the capsule 200, the control circuitry may instruct the power source to supply an electric current to the first heater 310 and the second heater 320. The instruction to supply an electric current from the power source may be in response to a manual operation (e.g., button-activation) or an automatic operation (e.g., puff-activation). As a result of the electric current, the capsule 200 may be conductively heated by the first heater 310 and the second heater 320 to generate an aerosol. The aerosol generated within the capsule 200 may pass through the second coupler 350 and, optionally, be drawn from the aerosol-generating device 300 via a mouthpiece.

Using the capsules and devices disclosed herein, an aerosol-forming substrate may be heated to generate an aerosol. In an example embodiment, a method of generating an aerosol may include engaging a capsule 200 between a first heater 310 and a second heater 320. The capsule 200 may define internal channels holding an aerosol-forming substrate. The method may additionally include heating the aerosol-forming substrate via conduction with the first heater 310 and the second heater 320. Furthermore, the incoming air entering the capsule 200 may optionally be heated air so as to also promote a heating of the aerosol-forming substrate via convection. Thus, the aerosol-forming substrate may be heated conductively and/or convectively to generate an aerosol.

Further to the non-limiting embodiments set forth herein, additional details of the substrates, capsules, devices, and methods discussed herein may also be found in U.S. application Ser. No. 16/451,662, filed Jun. 25, 2019, titled "CAPSULES, HEAT-NOT-BURN (HNB) AEROSOL-GENERATING DEVICES, AND METHODS OF GENERATING AN AEROSOL,"; U.S. application Ser. No. 16/252,951, filed Jan. 21, 2019, titled "CAPSULES, HEAT-NOT-BURN (HNB) AEROSOL-GENERATING DEVICES, AND METHODS OF GENERATING AN AEROSOL,"; U.S. application Ser. No. 15/845,501, filed Dec. 18, 2017, titled "VAPORIZING DEVICES AND METHODS FOR DELIVERING A COMPOUND USING THE SAME,"; and U.S. application Ser. No. 15/559,308, filed Sep. 18, 2017, titled "VAPORIZER FOR VAPORIZING AN ACTIVE INGREDIENT,", the disclosures of each of which are incorporated herein in their entirety by reference.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A capsule for an aerosol-generating device, comprising:
a housing defining inlet openings, outlet openings, and internal channels between the inlet openings and the outlet openings, the internal channels configured to hold an aerosol-forming substrate, the housing configured to facilitate a heating of the aerosol-forming substrate via conduction so as to generate an aerosol, the housing including a corrugated structure and a conductive cover, the corrugated structure having alternating ridges and furrows which, in combination with the conductive cover, defines the internal channels.

2. The capsule of claim 1, wherein the inlet openings are configured to permit air to enter the capsule, and the outlet openings are configured to permit the aerosol to exit the capsule.

3. The capsule of claim 1, wherein the internal channels are separate and independent conduits.

4. The capsule of claim 1, wherein the housing includes a body section, a first end cap, and a second end cap.

5. The capsule of claim 4, wherein the first end cap is secured to an upstream end of the body section, and the second end cap is secured to a downstream end of the body section.

6. The capsule of claim 4, wherein the body section defines the internal channels, the first end cap defines the inlet openings, and the second end cap defines the outlet openings.

7. The capsule of claim 6, wherein the first end cap and the second end cap are configured to engage with the body section such that each of the inlet openings of the first end cap is in fluidic communication with a corresponding outlet opening of the second end cap via a corresponding internal channel of the body section.

8. The capsule of claim 4, wherein the body section includes the corrugated structure and the conductive cover configured to contain the corrugated structure.

9. The capsule of claim 1, wherein each of the ridges and furrows has a coplanar surface between a pair of angled surfaces.

10. The capsule of claim 1, wherein the conductive cover is configured to surround the ridges and furrows of the corrugated structure.

11. The capsule of claim 8, wherein the corrugated structure has a portion with a cross-section resembling a trapezoidal wave.

12. The capsule of claim 8, wherein the conductive cover is in a form of a box sleeve.

13. The capsule of claim 8, wherein the conductive cover is made of a metal.

14. The capsule of claim 13, wherein the metal includes aluminum.

15. The capsule of claim 1, wherein the housing is configured such that the internal channels extend along a longest dimension of the housing.

16. The capsule of claim 1, wherein the housing has a length, a width, and a thickness, the length is greater than the width, the width is greater than the thickness, and the internal channels extend in a direction of the length.

17. The capsule of claim 1, wherein the aerosol-forming substrate includes a plant material.

18. The capsule of claim 17, wherein the plant material includes tobacco.

19. An aerosol-generating device, comprising:
a device body defining at least one slot configured to receive the capsule of claim 1 containing the aerosol-forming substrate, the device body including, a first side structure configured to partially define the at least one slot and receive the capsule therein, a second side structure opposite the first side structure, the second side structure being closed, and a heating assembly configured to heat the capsule containing the aerosol-forming substrate to generate an aerosol, the heating assembly including a first heater and a second heater configured to partially define the at least one slot in between so as to heat the aerosol-forming substrate via conduction when the capsule is received therein.

20. A method of generating an aerosol, comprising:

engaging the capsule of claim 1 within a slot defined by a first heater and a second heater, the capsule engaging with the slot such that the internal channels are sandwiched between the first heater and the second heater; and heating the aerosol-forming substrate via conduction with the first heater and the second heater.

21. The capsule of claim 16, wherein the ridges and furrows alternate in direction of the width of the housing.

* * * * *